United States Patent [19]

Ondetti

[11] 4,296,113

[45] Oct. 20, 1981

[54] MERCAPTOACYL DERIVATIVES OF KETO SUBSTITUTED PROLINE AND PIPECOLIC ACID

[75] Inventor: Miguel A. Ondetti, Princeton, N.J.

[73] Assignee: E. R. Squibb & Sons, Inc., Princeton, N.J.

[21] Appl. No.: 112,004

[22] Filed: Jan. 14, 1980

[51] Int. Cl.³ .................... A61K 31/40; A61K 31/44; C07D 207/16; C07D 401/12
[52] U.S. Cl. ................... 424/246; 260/326.2; 260/326.25; 260/326.35; 260/326.36; 260/326.43; 424/238; 424/250; 424/251; 424/263; 424/274; 546/188; 546/193; 546/194; 546/212; 546/214; 546/221; 546/281
[58] Field of Search .............. 260/326.25, 326.35, 260/326.36, 326.2, 326.43; 546/281; 424/274, 263, 246

[56] References Cited

U.S. PATENT DOCUMENTS

| | | | |
|---|---|---|---|
| 3,192,206 | 6/1965 | Lunsford et al. | 260/326.35 |
| 4,046,889 | 9/1977 | Ondetti et al. | 260/326.2 |
| 4,105,776 | 8/1978 | Ondetti et al. | 260/326.25 |
| 4,116,962 | 9/1978 | Ondetti et al. | 260/326.25 |
| 4,154,840 | 5/1979 | Ondetti et al. | 260/293.85 |
| 4,154,935 | 5/1979 | Ondetti et al. | 260/293.85 |
| 4,234,489 | 11/1980 | Ondetti et al. | 260/326.2 |

FOREIGN PATENT DOCUMENTS 1323061 7/1973 United Kingdom .......... 260/326.25

OTHER PUBLICATIONS

Patchett et al., JACS, 79, pp. 185–192, (1957).
Witkop et al., JACS, 79, pp. 192–197, (1957).
Baer et al., Can. J. Biochem. Physiol., 37, pp. 583–587, (1959).
Jolles et al., Bull. Soc. Chem., 1965(8), pp. 2253–2259.
Andreatta et al., Aust. J. Chem., 20, pp. 1493–1509, (1967).
Chem. Abstracts, 8th Coll. Index, 24416s–24417s, (1976).

*Primary Examiner*—Alton D. Rollins
*Attorney, Agent, or Firm*—Lawrence S. Levinson; Stephen B. Davis

[57] ABSTRACT

This invention is directed to compounds of the formula

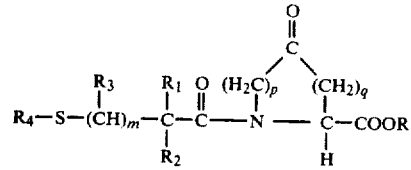

which are useful in the treatment of hypertension.

20 Claims, No Drawings

MERCAPTOACYL DERIVATIVES OF KETO SUBSTITUTED PROLINE AND PIPECOLIC ACID

RELATED APPLICATIONS

Krapcho in U.S. Ser. No. 99,164 discloses certain acylmercaptoacyl 4-ketoprolines as intermediates in the preparation of ketal and thioketal derivatives of mercaptoacyl prolines.

BACKGROUND OF THE INVENTION

Mercaptoacyl derivatives of proline and pipecolic acid are disclosed as useful antihypertension agents due to their angiotensin converting enzyme inhibition activity in U.S. Pat. No. 4,105,776 of Ondetti et al.

Mercaptoacyl derivatives and proline and pipecolic acid wherein the acyl sidechain can be substituted by an alkyl or trifluoromethyl group and the ring can be substituted with one or more halogens are also useful as angiotensin converting enzyme inhibitors as note Ondetti et al. U.S. Pat. No. 4,154,935.

Mercaptoacyl derivatives of proline and pipecolic acid wherein the acyl sidechain can be substituted with a lower alkylthio group are also disclosed as angiotensin converting enzyme inhibitors by Ondetti et al. in U.S. Pat. No. 4,116,962.

SUMMARY OF THE INVENTION

This invention relates to keto derivatives of mercaptoacyl proline and pipecolic acid of formula I and salts thereof $$R_4-S-(CH)_m-\underset{\underset{R_2}{|}}{\overset{\overset{R_3}{|}}{C}}-\underset{\overset{R_1}{|}}{\overset{O}{\underset{\|}{C}}}-N\overset{(H_2C)_p\diagdown\overset{O}{\underset{\|}{C}}\diagup(CH_2)_q}{\phantom{XXX}}\underset{\underset{H}{|}*}{C}-COOR. \qquad (I)$$

R and $R_2$ are independently selected from hydrogen and lower alkyl provided that $R_2$ is lower alkyl only if $R_1$ is also lower alkyl.

$R_1$ and $R_3$ are independently selected from hydrogen, lower alkyl, lower alkylthio, $-(CH_2)_n-SH$, and halo substituted lower alkyl.

$R_4$ is hydrogen, a hydrolyzably removable protecting group, a chemically removable protecting group, or when $R_1$ and $R_3$ are other than $-(CH_2)_n-SH$ a sulfide of the formula $$-S-(CH)_m-\underset{\underset{R_2}{|}}{\overset{\overset{R_3}{|}}{C}}-\underset{\overset{R_1}{|}}{\overset{O}{\underset{\|}{C}}}-N\overset{(H_2C)_p\diagdown\overset{O}{\underset{\|}{C}}\diagup(CH_2)_q}{\phantom{XXX}}\underset{\underset{H}{|}*}{C}-COOR$$

m is zero, one or two.

n is one, two or three p and q are each one or two provided that both are not two.

The asterisk in the above formula indicates a center of asymmetry in the ring. In the case of proline, i.e., p and q are both one, this center is in the L-configuration. In the case of pipecolic acid, i.e., one of p and q is two, this center is in the D,L or L-configuration.

Asymmetric centers can also be present in the mercaptoacyl sidechain depending upon the definition of $R_1$, $R_2$ and $R_3$. The products can accordingly exist in stereoisomeric forms or as racemic mixtures thereof. All of these are within the scope of the invention. The synthesis described below can utilize the racemate or one of the enantiomers as starting materials. When the racemic starting material is used in the synthesis procedure, the stereoisomers obtained in final product can be separated by conventional chromatographic or fractional crystallization methods. Preferably, if there is an asymmetric center in the mercaptoacyl sidechain, it is in the D-configuration.

DETAILED DESCRIPTION OF THE INVENTION

This invention in its broadest aspects relates to the mercaptoacyl derivatives of proline and pipecolic acid having formula I above and to salts thereof, to compositions containing such compounds and to the method for using such compounds as anti-hypertensive agents.

The term lower alkyl as used in defining the symbols R, $R_1$, $R_2$, and $R_3$ are straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl being most preferred. Similarly, the terms lower alkoxy and lower alkylthio refer to such lower alkyl groups attached to an oxygen or sulfur.

The term halo substituted lower alkyl refers to such lower alkyl groups described above in which one or more hydrogens have been replaced by chloro, bromo or fluoro groups such as trifluoromethyl, pentafluoroethyl, 2,2,2-trichloroethyl, chloromethyl, bromomethyl, etc.

The term hydrolyzably removable protecting group employed in defining $R_4$ refers to a group that can be removed by conventional hydrolysis or ammonolysis. Acyl groups of the formula $$R_5-\overset{O}{\underset{\|}{C}}-$$

are suitable for this purpose wherein $R_5$ can be lower alkyl of 1 to 7 carbons, lower alkyl substituted with one or more chloro, bromo or fluoro groups, $-(CH_2)_r$—cycloalkyl wherein the term cycloalkyl refers to saturated rings of 3 to 7 carbon atoms, preferably cyclohexyl, an aryl group such as $$-(CH_2)_r-\underset{R_6}{\bigcirc}\quad,$$

a hetero group such as $$-(CH_2)_r-\underset{X}{\bigcirc}\!\!\!\!\Big],\ \text{or}\ -(CH_2)_r-\underset{N}{\bigcirc}$$

wherein r is zero, one, two or three; $R_6$ is hydrogen, lower alkyl of 1 to 4 carbons, especially methyl, lower alkoxy of 1 to 4 carbons, especially methoxy, lower alkylthio of 1 to 4 carbons, especially methylthio, chloro, bromo, fluoro, trifluoromethyl, or hydroxy; and X is oxygen or sulfur. Preferred groups are the lower alkanoyl groups having up to four carbons, especially acetyl, and benzoyl.

The term chemically removable protecting group employed in defining $R_4$ refers to groups such as p-methoxybenzyl, trityl, etc. These groups can be removed after the completion of the acylation reaction by various means such as by treatment with trifluoroacetic acid and anisole.

Preferred compounds of formula I are the L-proline containing derivative, i.e., p and q are both one, and R is hydrogen.

With respect to the mercaptoacyl sidechain, preferred as final products are those compounds wherein $R_4$ is hydrogen; m is zero or one; $R_3$ is hydrogen; and $R_1$ and $R_2$ are both lower alkyl of 1 to 4 carbons, especially both methyl, or $R_2$ is hydrogen and $R_1$ is hydrogen, lower alkyl of 1 to 4 carbons, especially methyl, trifluoromethyl, methylthio, or mercaptomethyl. Also preferred as both intermediates and final products are the above sidechains wherein $R_4$ is lower alkanoyl of 1 to 4 carbons, especially acetyl, or benzoyl.

Especially preferred as final products are the compounds of formula I having the mercaptoacyl sidechain wherein $R_4$ is hydrogen; m is one; $R_3$ and $R_1$ are hydrogen; $R_2$ is methyl or hydrogen; and when $R_2$ is methyl the asymmetric carbon atom to which $R_2$ is attached is in the D-configuration.

The compounds of formula I are obtained by coupling the substituted proline or pipecolic acid of the formula

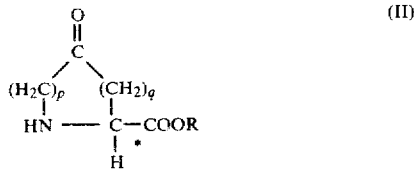

with an acid or its chemical equivalent of the formula

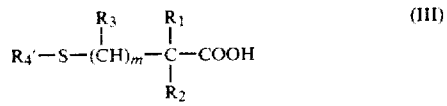

wherein $R_4'$ is hydrogen, a hydrolyzably or chemically removable protecting group to yield the product of the formula

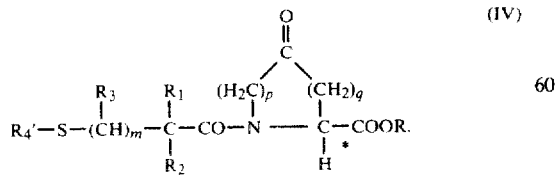

This reaction can be effected in the presence of a coupling agent such as dicyclohexylcarbodiimide or the like, or the acid can be activated by formation of its mixed anhydride, symmetrical anhydride, acid halide, active ester or use of Woodward reagent K, N-ethoxycarbonyl-2-ethoxy-1,2-dihydroquinoline or the like. For a review of the methods or acylation, see Methoden der Organishchen Chemie (Houben-Weyl), Vol. XV, part II, page 1 et seq. (1974). Preferably, the acid halide, especially the acid chloride, of formula III is reacted with the acid of formula II.

If the proline or pipecolic acid of formula II is reacted in the ester form the resulting ester product can be converted to the free acid, i.e., R is hydrogen, by conventional means. For example, if R is ethyl this ester protecting group can be removed by saponification.

The product of formula IV is preferably isolated and purified by crystallization, e.g., by forming the dicyclohexylamine salt and then converting the salt to the free acid form by treatment with an aqueous solution of an acid, such as potassium acid sulfate.

The product of formula IV bearing the acyl group $R_5$—CO— can be converted to the products of formula I wherein $R_4$ is hydrogen by conventional hydrolysis or by ammonolysis.

The products of formula I wherein $R_1$ and $R_3$ are other than —(CH$_2$)$_{n13}$ SH and $R_4$ is

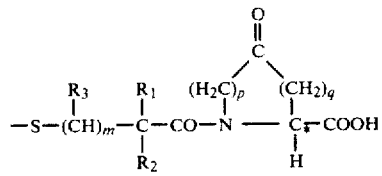

are obtained by directly oxidizing with iodine a product of formula I wherein $R_4$ is hydrogen.

The esters of formula I wherein R is lower alkyl can be obtained from the carboxylic acid compounds, i.e., wherein R is hydrogen, by conventional esterification procedures, e.g., by esterification with a diazoalkane such as diazomethane, a 1-alkyl-3-p-tolyltriazene, such as 1-n-butyl-3-p-tolyltriazene, or the like.

The compounds of formula I wherein $R_4$ is hydrogen or

can also be prepared by treating a dimethoxy compound of the formula

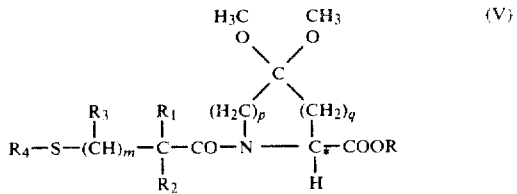

with an aqueous solution of hydrochloric acid at room temperature.

The compounds of formula V are disclosed in Krapcho U.S. Ser. No. 99,164. As set forth therein, an N-carbobenzyloxy keto substituted proline or pipecolic acid of formula II is treated with methanol in the presence of trimethyl orthoformate and concentrated sulfuric acid and the N-protecting group is then removed by hydrogenolysis in the presence of a palladium carbon catalyst to yield the dimethoxy intermediate of the formula

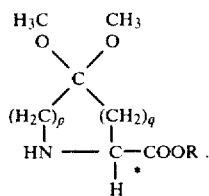

The intermediate of formula VI is then coupled with an acid or its chemical equivalent of formula III to yield the dimethoxy compounds of formula V.

Reference is also made to the following publications for additional illustrative methodology for producing starting materials and intermediates: U.S. Pat. Nos. 4,046,889, 4,105,776, 4,154,935 and 4,116,962; Can. J. Biochem. & Physiol. 37, 583-587, (1959); JACS 79, p. 185-192, (1957); JACS 79, p. 192-197, (1957); Bull. Soc. Chem., 1965(8), p. 2253-2259; and Aus. J. Chem. 20, p. 1493-1509, (1967).

The procedures illustrated therein can be utilized as general methods for the synthesis of compounds and separation of isomers which can be utilized in the invention described in this application. Additional illustrative details are found in the examples which serve as models for the preparation of other members of the group.

The compounds of this invention form basic salts with a variety of inorganic or organic bases. The salt forming ion derived from such bases can be metal ions, e.g., aluminum, alkali metal ions, such as sodium or potassium, alkaline earth metal ions such as calcium or magnesium, or an amine salt ion, of which a number are known for this purpose, for example, aralkylamines like dibenzylamine, N,N-dibenzylethylenediamine, lower alkylamines like methylamine, t-butylamine, procaine, lower alkylpiperidines like N-ethylpiperidine, cycloalkylamines, like cyclohexylamine or dicyclohexylamine, 1-adamantanamine, benzathine, or salts derived from amino acids like arginine, lysine or the like. The physiologically acceptable salts like the sodium or potassium salts can be used medicinally as described below and are preferred. These and other salts which are not necessarily physiologically acceptable are useful in isolating or purifying a product acceptable for the purposes described below, as illustrated with the dicyclohexylamine salt in the examples. The salts are produced by reacting the acid form of the compound with a equivalent of the base supplying the desired basic ion in a medium in which the salt precipitates or in aqueous medium and then lyophilizing. The free acid form can be obtained from the salt by conventional neutralization techniques, e.g., with potassium bisulfate, hydrochloric acid, etc.

The compound of formula I wherein $R_4$ is hydrogen,

or the disulfide type substituent, especially wherein $R_4$ is hydrogen, are useful as hypotensive agents. They inhibit the conversion of the decapeptide angiotensin I to angiotensin II and, therefore, are useful in relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen (renin) angiotensin I→(ACE)→angiotensin II sequence by inhibiting angiotensin converting enzyme and reducing or eliminating the formation of the pressor substance angiotensin II. Thus by the administration of a composition containing one, or a combination of compounds of formula I angiotensin dependent hypertension in the species of mammal suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises (for a 70 kg. mammal) a total daily dosage of about 30 to 600 mg., preferably about 30 to 300 mg., of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorothiazide, flumethiazide, hydroflumethiazide, benzdroflumethiazide, methchlothiazide, trichlormethiazide, polythiazide or benzthiazide, as well as ethacrynic acid, ticrynafen, chlorthalidone, furosemide, musolimine, bumetanide, triamterene, amiloride and spironolactone, and salts of such compounds.

The compounds of formula I can be formulated for use in the reduction of blood pressure in compositions such as tablets, capsules or elixirs for oral administration or in sterile solutions or suspensions for parenteral administration. About 10 to 500 mg. of a compound or mixture of compounds of formula I is compounded with a physiologically acceptble vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative process details are set forth in the following examples for the various reactions. These examples are preferred embodiments and also serve as models for the preparation of other compounds of this invention. The temperatures are given in degrees on the centigrade scale.

EXAMPLE 1

1-[3-(Acetylthio)-1-oxopropyl]-4-oxo-L-proline (a) N-Carbobenzyloxy-4-hydroxy-L-proline 26.5 g. (0.02 mole) of 4-hydroxy-L-proline and 34 ml. (0.23 mole) of benzyl chloroformate are reacted in 200 ml. of water and 100 ml. of acetone in the presence of 20 g. (0.02 mole) of potassium bicarbonate and 69 g. (0.50 mole) of potassium carbonate and worked up 90 ml. of concentrated hydrochloric acid as described in Can.J. Biochem. & Physiol. 37, 584 (1959) to obtain N-carbobenzyloxy-4-hydroxy-L-proline. This product is reacted with cyclohexylamine to form the cyclohexylamine salt yield 69 g., m.p. 193°-195°. The salt (34 g.) is neutralized with N-hydrochloric acid to obtain 27 g. of free acid as a colorless glass $[\alpha]_D^{26}$ −70°, (c, 1% in chloroform).

(b) N-carbobenzyloxy-4-keto-L-proline 21.5 g. (0.81 mole) of N-carbobenzyloxy-4-hydroxy-L-proline is oxidized in 1.2 liters of acetone with 83 ml. of 8 N chromic acid in sulfuric acid as described in J.A.C.S.79, 189 (1957). In order to facilitate the subsequent filtration of chromium salts, 30 g. of Celite (diatomaceous earth) is added to the acetone solution before introduction of the oxidizing agent. An air stirrer is employed. The reaction mixture is filtered and the acetone filtrate is concentrated to approximately 300 ml. before diluting with 1 liter of chloroform. The solution is washed with 300 ml. of saturated sodium chloride (four times), dried (MgSO$_4$), filtered and the solvent evaporated to give N-carbobenzyloxy-4-keto-L-proline (22.8 g.) which is crystallized from ether (50 ml.)-hexane (150 ml.) to obtain 17.2 g. (81%) of product, m.p. 99°-101°, $[\alpha]_D^{26}$ +17° (c, 1% in chloroform).

(c) 4-Keto-L-proline, hydrobromide

To 4.0 g. (0.015 mole) of N-carbobenzyloxy-4-keto-L-proline are added 20 ml. of hydrogen bromide in acetic acid (30–32%). The mixture is frequently swirled over a period of eight minutes. At the end of this period (effervescence has stopped), the yellow-orange solution is layered over with 250 ml. of ether, triturating the gummy product. The ether is discarded and the resulting tacky solid is triturated with fresh ether and finally with 50 ml. of acetonitrile to give 4-keto-L-proline, hydrobromide as a crystalline solid weighing 2.7 g. (85%), m.p. 153°-155° (dec.,), $[\alpha]_D^{26}$ −49° (c, 1% in water).

(d) 1-[3-(Acetylthio)-1-oxopropyl]-4-oxo-L-proline

A stirred solution of 4.1 g. (0.0195 mole) of 4-keto-L-proline, hydrobromide in 50 ml. of water is cooled to 5° and treated portionwise with solid sodium carbonate (foaming is controlled by adding a few drops of ether) to pH 8.0 (approx. 2 g. required). Then while continuing stirring and cooling, a solution of 3.5 g. (0.012 mole) of 3-acetylthiopropionyl chloride in 5 ml. of ethyl acetate is added portionwise by means of a pipette while maintaining the pH at 7.0-8.0 by dropwise addition of 25% (w/v) sodium carbonate solution (about 10 ml.). After about 10 minutes the pH stabilizes at 8.0-8.4. After continued stirring and cooling for a total of 1 hour, the solution is washed with ethyl acetate (2×50 ml.), layered over with 50 ml. of ethyl acetate, stirred, cooled, acidified carefully with concentrated hydrochloric acid to pH 2.0, saturated with sodium chloride, and the layers are separated. The aqueous phase is extracted with additional ethyl acetate (3×50 ml.), the combined organic layers dried (MgSO$_4$) and the solvent evaporated, finally at 0.2 mm. to give 4.8 g. of a yellow-orange glass-like residue. This residue is dissolved in 35 ml. of ethyl acetate and treated with a solution of 3.5 g. of dicyclohexylamine in 5 ml. of ethyl acetate. On seeding and rubbing, crystalline 1-[3-(acetylthio-1-oxopropyl)]-4-oxo-L-proline dicyclohexylamine salt separates, weight after cooling overnight, 2.7 g. (nearly colorless), m.p. 191°-193° (dec.), $[\alpha]_D^{26}$ −24° (c, 1% in CHCl$_3$).

This dicyclohexylamine salt is converted to the free acid by suspending it in ethyl acetate and treating with 45 ml. of 10% potassium bisulfate and stirring until two layers are obtained. After separating, the aqueous phase is extracted with ethyl acetate (4×75 ml.), the organic layers are combined, dried (MgSO$_4$) and the solvent is evaporated to give 3.7 g. of light yellow glass-like material.

Anal. Calc'd. for C$_{10}$H$_{13}$NO$_5$S: C, 46.32; H, 5.05; N, 5.40; S, 12.37. Found: C, 47.05; H, 5.50; N, 5.18; S, 12.07.

EXAMPLE 2

1-(3-Mercapto-1-oxopropyl)-4-oxo-L-proline

Argon is passed through a cold solution of 9 ml. of concentrated ammonia hydroxide in 22 ml. of water for 30 minutes. This material is then added while cooling and under a blanket of argon to 3.65 g. (0.014 mole) of 1-[3-(acetylthio)-1-oxopropyl]-4-oxo-L-proline. Approximately 30 minutes are required to dissolve the proline starting with the aid of a magnetic stirrer. Stirring under argon is continued at room temperature for an additional two hours after which the solution is extracted with 30 ml. of ethyl acetate (this and subsequent operations are carried out as much as possible under an argon atmosphere). The aqueous layer is cooled, stirred, layered over with 30 ml. of ethyl acetate, and acidified portionwise with 1:1 HCl. Sodium chloride is added, the layers are separated, and the aqueous phase is extracted with additional ethyl acetate (3×30 ml.). A brown gummy fraction remains insoluble in either phase. After drying over MgSO$_4$ the combined ethyl acetate layers are evaporated to give a mostly solid residue which becomes an amorphous solid when triturated with ether and the evaporation repeated to yield 1.4 g. of pale yellow material.

1.3 g. of this material is rubbed under 50 ml. of ether, cooled under argon for one hour, filtered, washed with ether, and dried in vacuo to yield 1.0 g. of 1-(3-mercapto-1-oxopropyl)-4-oxo-L-proline, R$_f$ 0.67 (methanol on silica gel, visualized in iodine vapor).

Anal. Calc'd. for C$_8$H$_{11}$NO$_4$S. 0.5 H$_2$O: C, 42.46; H, 5.35; N, 6.19; S, 13.71. Found: C, 42.66; H, 5.39; N, 6.30; S, 13.30.

EXAMPLE 3

(S)-1-[(3-Acetylthio)-2-methyl-1-oxopropyl]-4-oxo-L-proline

Following the procedure of Example 1 but substituting D-3-acetylthio-2-methylpropionyl chloride for the 3-acetylthio propionyl chloride, one obtains (S)-1-[(3-acetylthio)-2-methyl-1-oxopropyl]-4-oxo-L-proline.

EXAMPLE 4

(S)-1-(3-Mercapto-2-methyl-1-oxopropyl)-4-oxo-L-proline

The product from Example 3 is treated with ammonia hydroxide according to the procedure of Example 2 to yield (S)-1-(3-mercapto-2-methyl-1-oxopropyl)-4-oxo-L-proline.

EXAMPLE 5

1-[(3-Acetylthio)-2-trifluoromethyl-1-oxopropyl]-4-oxo-L-proline (a) D,L-3-(Acetylthio)-2-trifluoromethylpropionic acid α-Trifluoromethyl acrylic acid (10 g., 0.071 mole) [prepared according to the procedure set forth in J.

Chem. Soc., 1954, p. 371] is cooled in a salt-ice-water bath, stirred and treated portionwise with 5.7 ml. (0.075 mole) of 97% thiolacetic acid. After the addition, the yellow liquid is stirred in the cold for one hour, allowed to warm to room temperature, and distilled to yield 14 g. (91%) of D,L-3-(acetylthio)-2-trifluoromethylpropionic acid as a light yellow oil, b.p. 149°-153°/13 mm. The material solidifies on storing in the cold.

(b) D,L-3-(Acetylthio)-2-trifluoromethylpropionyl chloride

The D,L-3-(acetylthio)-2-trifluoromethylpropionyl acid (7 g., 0.032 mole) is treated with 18 ml. (0.25) of redistilled thionyl chloride and the mixture is refluxed for three hours. After removing the excess thionyl chloride on a rotary evaporator, the residue is distilled to give 6.8 g. of D,L-3-(acetylthio)-2-trifluoromethylpropionyl chloride as a pale yellow oil; b.p. 80°-82°/16 mm.

(c) 1-[(3-Acetylthio)-2-trifluoromethyl-1-oxopropyl]-4-oxo-L-proline

The D,L-3-(acetylthio)-2-trifluoromethylpropionyl chloride is reacted with 4-keto-L-proline, hydrobromide according to the procedure of Example 1 (d) to yield 1-[(3-acetylthio)-2-trifluoromethyl-1-oxopropyl]-4-oxo-1-proline. This mixture of diastereoisomers can then be separated by conventional techniques.

EXAMPLE 6

1-(3-Mercapto-2-trifluoromethyl-1-oxopropyl)-4-oxo-L-proline

The product from Example 5 (in the form of the diastereoisomer mixture or as the separated isomers) is hydrolyzed with concentrated ammonia according to the procedure of Example 2 to yield 1-(3-mercapto-2-trifluoromethyl-1-oxopropyl)-4-oxo-L-proline.

EXAMPLE 7

(S)-1-(3-Mercapto-2-mercaptomethyl-1-oxopropyl)-4-oxo-L-proline (a) (S)-1-[3-(Acetylthio)-2-(acetylthiomethyl)-1-oxopropyl]-4-oxo-L-proline Following the procedure of Example 1 but substituting D-3-acetylthiomethyl-3-acetylthiopropionyl chloride for the 3-acetylthiopropionyl chloride in part (d), one obtains (S)-1-[3-(acetylthio)-2-(acetylthiomethyl)-1-oxopropyl]-4-oxo-L-proline.

(b) (S)-1-(3-Mercapto-2-mercaptomethyl-1-oxopropyl)-4-oxo-L-proline

The product from part (a) is hydrolyzed with concentrated ammonia according to the procedure of Example 2 to yield (S)-1-(3-mercapto-2-mercaptomethyl-1-oxopropyl)-4-oxo-L-proline.

EXAMPLE 8

1-(3-Mercapto-2-methylthio-1-oxopropyl)-4-oxo-L-proline (a) 3-(Acetylthio)-2-(methylthio)propionic acid 12.5 g. (0.094 mole) of methyl-2-(methylthio)acrylate [prepared from methyl 2-chloroacrylate according to the procedure of Gundesmann et al., Chemische Berichte 94, 3254 (1916)] is stirred with 1 N aqueous sodium hydroxide (94 ml.) with ice cooling. The mixture is allowed to warm to ambient temperature, then stirred for five hours. The resulting solution is washed with ether, then acidified to pH 2 with concentrated hydrochloric acid. The solid precipitate is extracted into methylene chloride, and the solution is washed with saturated sodium chloride and the solvent evaporated. The solid residue, 2-(methylthio)acrylic acid; m.p. 70°-75°, is used immediately in the following reaction.

Equimolar amounts of 2-(methylthio)acrylic acid and thiolacetic acid are mixed under argon and stirred at 80° for several hours to yield 3-(acetylthio)-2-methylthio)-propionic acid.

(b) 3-(Acetylthio)-2-(methylthio)propionic acid chloride

The 3-(acetylthio)-2-(methylthio)propionic acid is refluxed in thionyl chloride for two hours. The reaction mixture is distilled to remove excess thionyl chloride and the product is distilled in vacuo to yield 3-(acetylthio)-2-(methylthio)propionic acid chloride.

(c) 1-[3-(Acetylthio)-2-methylthio-1-oxopropyl]-4-oxo-L-proline

The 3-(acetylthio)-2-(methylthio)propionic acid chloride is reacted with 4-keto-L-proline, hydrobromide according to the procedure of Example 1 (d) to yield 1-[3-(acetylthio)-2-methylthio-1-oxopropyl]-4-oxo-L-proline.

(d) 1-(3-Mercapto-2-methylthio-1-oxopropyl)-4-oxo-L-proline

The product from part (c) is hydrolyzed with concentrated ammonia according to the procedure of Example 2 to yield 1-(3-mercapto-2-methylthio-1-oxopropyl)-4-oxo-L-proline.

EXAMPLE 9

1-(4-Mercapto-1-oxobutyl)-4-oxo-L-proline (a) 1-[4-(Acetylthio)-1-oxobutyl]-4-oxo-L-proline Following the procedure of Example 1 but substituting 4-acetylthiobutyroyl chloride for the 3-acetylthiopropionyl chloride in part (d), one obtains 1-[4-(acetylthio)-1-oxobutyl]-4-oxo-L-proline.

(b) 1-(4-Mercapto-1-oxobutyl)-4-oxo-L-proline

The product form part (a) is hydrolyzed with concentrated ammonia according to the procedure of Example 2 to yield 1-(4-mercapto-1-oxobutyl)-4-oxo-L-proline.

EXAMPLE 10

1-(2-Mercapto-1-oxoethyl)-4-oxo-L-proline (a) 1-[2-(Acetylthio)-1-oxoethyl]-4-oxo-L-proline Following the procedure of Example 1 but substituting acetylthioacetyl chloride for the 3-acetylthiopropionyl chloride in part (d), one obtains 1-[2-acetylthio)-1-oxoethyl]-4-oxo-L-proline.

(b) 1-(2-Mercapto-1-oxoethyl)-4-oxo-L-proline

The product from part (a) is hydrolyzed with concentrated ammonia according to the procedure of Example 2 to yield 1-(2-mercapto-1-oxoethyl)-4-oxo-L-proline.

EXAMPLE 11

1-(3-Mercapto-2,2-dimethyl-1-oxopropyl)-4-oxo-L-proline (a) 1-[3-(Acethylthio)-2,2-dimethyl-1-oxopropyl]-4-oxo-L-proline Following the procedure of Example 1 but substituting 3-acetylthio-2,2-dimethylpropionyl chloride for the 3-acetylthiopropionyl chloride in part (d), one obtains 1-[3-(acetylthio)-2,2-dimethyl-1-oxopropyl]-4-oxo-L-proline.

(b) 1-(3-Mercapto-2,2-dimethyl-1-oxopropyl)-4-oxo-L-proline

The product from part (a) is hydrolyzed with concentrated ammonia according to the procedure of Example to yield 1-(3-mercapto-2,2-dimethyl-1-oxopropyl)-4-oxo-L-proline.

EXAMPLE 12

(S)-1-(3-Mercapto-2-ethyl-1-oxopropyl)-4-oxo-L-proline (a) (S)-1-[3-(Acetylthio)-2-ethyl-1-oxopropyl]-4-oxo-L-proline Following the procedure of Example 1 but substituting D-3-acetylthio-2-ethylpropionyl chloride for the D-3-acetylthio-2-methylpropionyl chloride in part (d), one obtains (S)-1-[3-(acetylthio)-2-ethyl-1-oxopropyl]-4-oxo-L-proline.

(b) (S)-1-(3-Mercapto-2-ethyl-1-oxopropyl)-4-L-proline

The product from part (a) is hydrolyzed with concentrated ammonia according to the procedure of Example 2 to yield (S)-1-(3-mercapto-2-ethyl-1-oxopropyl)-4-oxo-L-proline.

EXAMPLE 13

1-(3-Mercapto-1-oxopropyl)-4-oxo-L-pipecolic acid (a) 1-[3-(Acetylthio)-1-oxopropyl]-4-oxo-L-pipecolic acid Following the procedure of Example 1 but substituting 4-keto-L-pipecolic acid for the 4-keto-L-proline in part (d), one obtains 1-[3-(acetylthio)-1-oxopropyl]-4-oxo-L-pipecolic acid.

(b) 1-(3-Mercapto-1-oxopropyl)-4-oxo-L-pipecolic acid

The product from part (a) is hydrolyzed with concentrated ammonia to yield 1-(3-mercapto-1-oxopropyl)-4-oxo-L-pipecolic acid.

EXAMPLE 14

(S)-1-(3-Mercapto-2-methyl-1-oxopropyl)-5-oxo-L-pipecolic acid (a) (S)-1-[3-(Acetylthio)-2-methyl-1-oxopropyl]-5-oxo-L-pipecolic acid Following the procedure of Example 1 but substituting 5-keto-L-pipecolic acid for the 4-keto-L-proline in part (d) and D-3-acetylthio-2-methylpropionyl chloride for the acetylthiopropionyl chloride in part (d), one obtains (S)-1-[3-(acetylthio)-2-methyl-1-oxopropyl]-5-keto-L-pipecolic acid.

(b) (S)-1-(3-Mercapto-2-methyl-1-oxopropyl)-5-keto-L-pipecolic acid

The product from part (a) is hydrolyzed with concentrated ammonia according to the procedure of Example 2 to yield (S)-1-(3-mercapto-2-methyl-1-oxopropyl)-5-keto-L-pipecolic acid.

EXAMPLE 15

1-(3-Mercapto-2-trifluoromethyl-1-oxopropyl)-4-oxo-L-proline (a) 3-[[(4-Methoxy)phenylmethyl]thio]-2-trifluoromethylpropionyl chloride A neat mixture of 1-trifluoromethylacrylic acid (3.9 g.) and 4-methoxybenzylthiol (4.3 g.) is stirred at 100°–110° for one hour. The mixture is allowed to cool to room temperature and the solid is recrystallized from cyclohexane to yield 3-[[(4-methoxy)phenylmethyl]thio]-2-trifluoromethylpropionic acid; m.p. 72°–74°.

Treatment of this acid with thionyl chloride yields 3-[[(4-methoxy)phenylmethyl]thio]-2-trifluoromethylpropionyl chloride.

(b) 1-[3-[[(4-Methoxy)phenylmethyl]thio]-2-trifluoromethyl-1-oxopropyl]-4-oxo-L-proline The 3-[[(4-methoxy)phenylmethyl]thio]-2-trifluoromethylpropionyl chloride from part (a) is reacted with 4-keto-L-proline to yield 1-[3-[[(4-methoxy)phenylmethyl]thio]-2-trifluoromethyl-1-oxopropyl]-4-oxo-L-proline.

(c) 1-(3-Mercapto-2-trifluoromethyl-1-oxopropyl)-4-oxo-L-proline

The product from part (b) is mixed with trifluoroacetic acid and anisole under nitrogen. The solvents are removed under vacuum to yield as a residue 1-(3-mercapto-2-trifluoromethyl-1-oxopro-yl)-4-oxo-L-proline.

EXAMPLE 16

(S)-1-(3-Mercapto-3-methyl-1-oxopropyl)-4-oxo-L-proline (a) (S)-1-[3-(Acetylthio)-3-methyl-1-oxopropyl]-4-oxo-L-proline Following the procedure of Example 1 but substituting D-3-acetylthio-3-methylpropionyl chloride for the 3-acetylthiopropionyl chloride in part (d), one obtains (S)-1-[3-(acetylthio)-3-methyl-1-oxopropyl]-4-oxo-L-proline.

(b) (S)-1-(3-Mercapto-3-methyl-1-oxopropyl)-4-oxo-L-proline

The product from part (a) is hydrolyzed with concentrated ammonia to yield (S)-1-(3-mercapto-3-methyl-1-oxopropyl)-4-oxo-L-proline.

EXAMPLES 17–25

Following the procedure of Example 1 but substituting for the 3-acetylthiopropionyl chloride the acid chloride listed below in Col. I one obtains the acylmercapto product listed below in Col. II.

| Col. I | Col. II |
| --- | --- |
| 3-benzoylthiopropionyl chloride | 1-[3-(benzoylthio)-1-oxopropyl]-4-oxo-L-proline |
| D-3-benzoylthio-2-methylpropionyl chloride | (S)-1-[3-(benzoylthio)-2-methyl-1-oxopropyl]-4-oxo-L-proline |
| D-3-[[(2-thienyl)-carbonyl]-thio]-2-methylpropionyl chloride | (S)-1-[3-[[(2-thienyl)carbonyl]thio]-2-methyl-1-oxopropyl]-4-oxo-L-proline |
| 3-[[(2,2,2-trichloroethyl)carbonyl]thio]propionyl chloride | 1-[3-[[(2,2,2-trichloroethyl)carbonyl]thio]-1-oxopropyl]-4-oxo-L-proline |
| D-3-[[(2-furyl)-carbonyl]thio]-2-methylpropionyl chloride | (S)-1-[3-[[(2-furyl)carbonyl]thio]-2-methyl-1-oxopropyl]-4-oxo-L-proline |
| 3-[[(4-pyridyl)-carbonyl]thio]-propionyl chloride | 1-[3-[[(4-pyridyl)carbonyl]thio]-1-oxopropyl]-4-oxo-L-proline |
| D-3-[[(4-methylphenyl)-carbonyl]-thio]-2-methylpropionyl chloride | (S)-1-[3-[[(4-methylphenyl)carbonyl]thio]-2-methyl-1-oxopropyl]-4-oxo-L-proline |
| 2-[[(phenylmethyl)-carbonyl]-acetyl chloride | 1-[2-[[(phenylmethyl)carbonyl]thio]-1-oxoethyl]-4-oxo-L-proline |
| 4-[[(cyclohexyl)-carbonyl]thio]-butyroyl chloride | 1-[4-[[(cyclohexyl)carbonyl]thio]-1-oxobutyl]-4-oxo-L-proline |

EXAMPLE 26

(S)-1-(3-Mercapto-2-methyl-1-oxopropyl)-4-oxo-L-proline, 1-adamantanamine salt The product of Example 4 can also be prepared according to the following procedure.

(a) N-Carbobenzyloxy-4,4-dimethoxy-L-proline, methyl ester

A stirred solution of 7.8 g. (0.03 mole) of N-carbobenzyloxy-4-keto-L-proline from Example 1 in 60 ml. of methanol is treated with 96 ml. of trimethyl orthoformate, followed by 0.6 ml. of concentrated sulfuric acid and allowed to stand overnight at room temperature.

The pale yellow solution is stirred, treated with 1.5 g. of potassium carbonate, followed by 30 ml. of water and the bulk of the solvent is removed on a rotary evaporator to give a syrupy residue which is shaken with 30 ml. of water and 30 ml. of chloroform. After separating the layers of aqueous phase is extracted with additional chloroform (3×30 ml.) and the combined organic layers are washed with 45 ml. of saturated sodium chloride solution and dried (MgSO$_4$). Evaporation of the solvent yields 8.4 g. (88%) of N-carbobenzyloxy-4,4-dimethoxy-L-proline, methyl ester.

(b) N-Carbobenzyloxy-4,4-dimethoxy-L-proline

The ester (8.4 g., 0.026 mole) from part (a) is dissolved in 80 ml. of methanol, treated dropwise at −1° to 4° with 18 ml. (0.036 mole) of 2 N sodium hydroxide kept at 0° for one hour, and at room temperature overnight. After removing about one half of the solvent on a rotary evaporator, the solution is diluted with 150 ml. of water, washed with 100 ml. of ether (wash discarded), acidified while cooling with 63 ml. of 1:1 hydrochloric acid to pH 2, and extracted with ethyl acetate (4×750 ml.). The combined extracts are washed with 50 ml. of saturated sodium chloride solution, dried (MgSO$_4$), and the solvent evaporated to give 8.0 g. of a pale yellow viscous oil. The oil is dissolved in 35 ml. ethanol, treated with 3.0 g of cyclohexylamine in 10 ml. of ethanol and diluted to 500 ml. with ether. On seeding and rubbing, the crystalline N-carbobenzyloxy-4,4-dimethoxy-L-proline cyclohexylamine salt separated; weight after cooling overnight, 7.0 g., m.p. 157°–159° (s, 151°) $[\alpha]_D^{26}$ −34° (c, 1% in EtOH). This material is recrystallized from 100 ml. of acetonitrile to give the salt as a colorless solid, m.p. 158°–160° (s, 154°) $[\alpha]_D^{26}$ −33° (c, 1% in EtOH).

The N-carbobenzyloxy-4,4-dimethoxy-L-proline cyclohexylamine salt is suspended in 40 ml. of ethyl acetate, stirred and treated with 25 ml. of 1 N hydrochloric acid. When two clear layers are obtained they are separated, the aqueous phase is extracted with additional ethyl acetate (3×40 ml.), the combined organic layers are dried (MgSO$_4$), and the solvent evaporated, finally at 0.2 mm and 40° to yield 7.2 g. (70%) of N-carbobenzyloxy-4,4-dimethoxy-L-proline as a pale yellow viscous syrup.

(c) 4,4-Dimethoxy-L-proline

A solution of N-carbobenzyloxy-4,4-dimethoxy-L-proline (72 g., 0.022 mole) in 210 ml. of methanol-water (2:1) is treated with 2.3 g. of 5% palladium-carbon and shaken on a Parr hydrogenator for 6 hours. The catalyst is filtered off under nitrogen, washed with methanol, and the combined filtrates are evaporated, finally at 0.1–0.2 mm., to give a partly crystalline residue. This residue is taken up in 200 ml. of methanol and the evaporation repeated. When the solid is rubbed under ether (evaporation again repeated) there is obtained 3.6 g. (95%) of nearly colorless 4,4-dimethoxy-L-proline, m.p. 192°–194° (dec.); $[\alpha]_D^{26}$ −47° (c, 1% in MeOH).

A sample crystallized from methanol-ether is colorless and melts at 197°–198° (dec.); $[\alpha]_D^{26}$ −49° (c, 1% in MeOH).

(d) (S)-1-[3-(Acetylthio)-2-methyl-1-oxopropyl]-4,4-dimethoxy-L-proline

A stirred solution of 3.3 g. (0.019 mole) of 4,4-dimethoxy-L-proline in 50 ml. of water is cooled to 5° and brought to pH 8.5 by the addition of 25% sodium carbonate solution (w/v). Then while continuing stirring and cooling, a solution of 3.8 g. (0.021 mole) of D-3-acetylthio-2-methylpropanoyl chloride in 5 ml. of ether is added portionwise while maintaining the pH at 7.5–8.5 by dropwise addition of 25% sodium carbonate solution. When the pH has stabilized at 8.2–8.4 (after about 15 minutes), stirring and cooling is continued for a total of one hour. The solution is then washed with 50 ml. of ethyl acetate (wash discarded), layered over with 50 ml. of ethyl acetate, cooled, stirred, acidified carefully with 1:1 hydrochloric acid to pH 2.0, saturated with sodium chloride, and the layers separated. The aqueous phase is extracted with additional ethyl acetate (3×50 ml.), the combined organic layers are dried (MgSO$_4$), and the solvent evaporated, finally at 0.2 mm to give 6.7 g. of syrupy product. This syrup is treated in 70 ml. of ethyl acetate with 3.9 g. of dicyclohexylamine to give 6.5 g. of colorless (S)-1-[3-(acetylthio)-2-methyl-1-oxopropyl]-4,4-dimethoxy-L-proline dicyclohexylamine salt in two crops (3.1 g. and 3.4 g.), m.p. 158°–160° (s, 145°). $[\alpha]_D^{26}$ −71° (c, 1% in EtOH).

Following recrystallization from 20 ml. of hot ethyl acetate-60 ml. of hexane, the colorless solid salt weighs 6.0 g., m.p. 158°–166° (s, 155°), $[\alpha]_D^{25}$ −69° (c, 1% in EtOH).

The dicyclohexylamine salt is converted to the free acid by suspending 5.0 g. in 50 ml. of ethyl acetate, cooling and treating with 60 ml. of 10% potassium bisulfate solution to give 2 clear layers. After separating, the aqueous phase is extracted with ethyl acetate (3×50 ml.), the combined organic layers are dried (MgSO$_4$), and the solvent evaporated, finally at 0.1–0.2 mm. and 45° to give 4.1 g. (69%) of (S)-1-[3-(acetylthio)-2-methyl-1-oxopropyl]-4,4-dimethoxy-L-proline as a viscous, almost glasslike material $[\alpha]_D^{25}$ −112° (c, 1% in EtOH).

(e) (S)-1-(3-Mercapto-2-methyl-1-oxopropyl)-4,4-dimethoxy-L-proline

Argon is passed through a cold solution of 8.5 ml. of concentrated ammonium hydroxide in 20 ml of water for 0.25 hour. The latter is then added while cooling and under a blanket of argon to 4.1 g. (0.013 mole) of (S)-1-[3-(acetylthio)-2-methyl-1-oxopropyl]-4,4-dimethoxy-L-proline and the mixture is swirled in an icebath until a pale yellow solution is obtained (about 15 minutes). Stirring under argon is continued at room temperature for an additional 2 hours, then the solution is extracted with 30 ml. of ethyl acetate (this and subsequent operations are carried out as much as possible under an argon atmosphere). The aqueous layer is cooled, stirred, layered over with 30 ml. of ethyl acetate, and acidified portionwise with approximately 16 ml. of 1:1 hydrochloric acid. The layers are separated, the aqueous phase is extracted with additional ethyl acetate (3×30 ml.), the combined ethyl acetate layers are dried (MgSO$_4$), and the solvent evaporated to give 3.5 g. (100%) of (S)-1-(3-mercapto-2-methyl-1-oxopropyl)-

4,4-dimethoxy-L-proline as a colorless, viscous syrup, $[\alpha]_D^{25}$ −72° (c, 1% in EtOH).

The latter (3.4 g.) is triturated with 20 ml. of ethyl acetate, rubbed, diluted with 30 ml. of hexane, and cooled to give a colorless solid, weight 2.6 g., m.p. 108°-110°, $[\alpha]_D^{25}$ −77° (c, 1% in EtOH).

(f) (S)-1-(3-Mercapto-2-methyl-1-oxopropyl)-4-oxo-L-proline, 1-adamantanamine salt The (S)-1-(3-mercapto-2-methyl-1-oxopropyl)-4,4-dimethoxy-L-proline (0.4 g., 0.0014 mole) is added to 8 ml. of stirred N HCl through which argon had previously been passed for ten minutes. After a solution is obtained, the flask is stoppered under argon and kept overnight at room temperature. The following steps are also carried out under an atmosphere of argon to the extent possible. To the stirred solution there is added 20 ml. of methylene chloride and after saturating with sodium chloride the layers are separated. The aqueous phase is extracted with additional methylene chloride (3×15 ml.), the organic layers are combined, dried (MgSO$_4$), and the solvents evaporated to give a foamy residue. Following trituration with ether (evaporation repeated), 0.26 g. of (S)-1-(3-mercapto-2-methyl-1-oxopropyl)-4-oxo-L-proline are obtained as an amorphous solid (hygroscopic).

0.245 g. of this product is dissolved in 7 ml. of acetonitrile and treated with 0.17 g. of 1-adamantanamine to precipitate the salt as a voluminous solid. After cooling overnight, the colorless material is filtered, washed with cold acetonitrile and ether, and dried in vacuo to yield 0.36 g. of (S)-1-(3-mercapto-2-methyl-1-oxopropyl)-4-oxo-L-proline, 1-adamantanamine salt (1:1); m.p. 188°-190° (dec.); s. 184°; $[\alpha]_D^{25}$ −13° (c, 1% in methanol).

Anal. Calc'd. for C$_9$H$_{13}$NO$_4$S.C$_{10}$H$_{17}$N.0.25H$_2$0: C, 58.96; H, 8.02; N, 7.24; S, 8.29. Found: C, 58.60; H, 8.37; N, 7.16; S, 8.29.

EXAMPLE 27

1,1'-[Dithiobis(1-oxo-3,1-propanediyl)]bis[4-oxo-L-proline]

The product from Example 2 is dissolved in water and the pH adjusted to 6.5 by the addition of 1 N sodium hydroxide. To this stirred solution is added dropwise a 0.5 M iodine solution in 95% ethanol (6.34 g. iodine/50 ml. solution) while maintaining the pH at 5.5 to 6.5 with 1 N sodium hydroxide. Excess iodine is removed with dilute sodium thiosulfate and the solution is concentrated, cooled and acidified with 1:1 hydrochloric acid. Solvent is added and the layers are separated. The organic layer is dried (MgSO$_4$) and the solvent evaporated to yield as a residue 1,1'-[dithiobis(1-oxo-3,1-propanediyl)]bis[4-oxo-L-proline].

EXAMPLE 28

1-[3-(Acetylthio)-1-oxopropyl]-4-oxo-L-proline, methyl ester

A solution of the product of Example 1 in ether is treated with a slight excess of diazomethane. After standing at room temperature for two hours, the solvent is evaporated to give 1-[3-(acetylthio)-1-oxopropyl]-4-oxo-L-proline, methyl ester.

EXAMPLE 29

1-(3-Mercapto-1-oxopropyl)-4-oxo-L-proline, methyl ester

The product from Example 28 is hydrolyzed with concentrated ammonia according to the procedure of Example 2 to yield 1-(3-mercapto-1-oxopropyl)-4-oxo-L-proline, methyl ester.

EXAMPLE 30

1-(3-Mercapto-1-oxopropyl)-4-oxo-L-proline, sodium salt

A solution of 1.0 g. of the product of Example 2 is dissolved in 10 ml. of water and treated with one equivalent of sodium bicarbonate. The solution is freeze-dried to give 1-(3-mercapto-1-oxopropyl)-4-oxo-L-proline, sodium salt.

In a similar manner, by employing potassium bicarbonate the corresponding potassium salt is obtained.

EXAMPLE 31

(S)-1-(3-Mercapto-2-methyl-1-oxopropyl)-4-oxo-L-proline, sodium salt

A solution of 1.0 g. of the product of Example 4 is dissolved in 10 ml. of water and treated with one equivalent of sodium bicarbonate. The solution is freeze-dried to give 1-(3-mercapto-2-methyl-1-oxopropyl)-4-oxo-L-proline, sodium salt.

In a similar manner, by employing potassium bicarbonate the corresponding potassium salt is obtained.

EXAMPLE 32

1000 tablets each containing the following ingredients:

| | | |
|---|---|---|
| 1-(3-mercapto-1-oxopropyl)-4-oxo-L-proline | 100 | mg. |
| Corn starch | 50 | mg. |
| Gelatin | 7.5 | mg. |
| Avicel (microcrystalline cellulose) | 25 | mg |
| Magnesium stearate | 2.5 | mg. |
| | 185 | mg. | are prepared (from sufficient bulk quantities) by mixing the 1-(3-mercapto-1-oxopropyl)-4-oxo-L-proline and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

EXAMPLE 33

Tablets each containing 100 mg. of (S)-1-(3-mercapto-2-methyl-1-oxopropyl)-4-oxo-L-proline are produced as described in Example 32.

EXAMPLE 34

1000 tablets each containing 50 mg. of 1-(3-mercapto-1-oxopropyl)-4-oxo-L-proline are produced from the following ingredients:

| | |
|---|---|
| 1-(3-mercapto-1-oxopropyl)-4-oxo-L-proline | 50 g. |
| Lactose | 100 g. |

| -continued | |
|---|---|
| Avicel | 150 g. |
| Corn starch | 50 g. |
| Magnesium stearate | 5 g. |

The 1-(3-mercapto-1-oxopropyl)-4-oxo-L-proline, lactose, and Avicel are admixed, and then blended with corn starch. Magnesium stearate is added. The dry mixture is compressed in a tablet press to form 1000 355 mg. tablets each containing 50 mg. of active ingredient. The tablets are coated with a solution of Methocel E 15 (methyl cellulose) including as a color a lake containing yellow #6.

EXAMPLE 35

Tablets each containing 50 mg. of (S)-1-(3-mercapto-2-methyl-1-oxopropyl)-4-oxo-L-proline are prepared as described in example 34.

EXAMPLE 36

Two piece #1 gelatin capsules each containing 100 mg. of 1-(3-mercapto-1-oxopropyl)-4-oxo-L-proline, sodium salt, are filled with a mixture of the following ingredients:

| | |
|---|---|
| 1-(3-mercapto-1-oxopropyl)-4-oxo-L-proline, sodium salt | 100 mg. |
| Magnesium stearate | 7 mg. |
| Lactose | 193 mg. |

EXAMPLE 37

Gelatin capsules containing 100 mg. of (S)-1-(3-mercapto-2-methyl-1-oxopropyl)-4-oxo-L-proline, sodium salt are prepared as described in Example 36.

EXAMPLE 38

An injectable solution is produced as follows:

| 1-(3-mercapto-1-oxopropyl)-4-oxo-L-proline | 500 | g. |
|---|---|---|
| Methyl paraben | 5 | g. |
| Propyl paraben | 1 | g. |
| Sodium chloride | 25 | g. |
| Water for injection qs. | 5 | l |

The active substance, preservatives and sodium chloride are dissolved in 3 liters of water and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

EXAMPLE 39

An injection solution containing (S)-1-(3-mercapto-2-methyl-1-oxopropyl)-4-oxo-L-proline is prepared as described in Example 38.

EXAMPLE 40

6000 tablets each containing the following ingredients:

| | |
|---|---|
| 1-(3-mercapto-1-oxopropyl)-4-oxo-L-proline | 100 mg. |

| -continued | |
|---|---|
| Avicel (microcrystalline cellulose) | 100 mg. |
| Hydrochlorothiazide | 12.5 mg. |
| Lactose U.S.P. | 113 mg. |
| Corn starch U.S.P. | 17.5 mg. |
| Stearic acid U.S.P. | 7 mg. |
| | 350 mg. | are produced from sufficient bulk quantities by slugging the 1-(3-mercapto-1-oxopropyl)-4-oxo-L-proline, Avicel, and a portion of the stearic acid. The slugs are ground and passed through a #2 screen, then mixed with the hydrochlorothiazide, lactose, corn starch and remainder of the stearic acid. The mixture is compressed into 350 mg. capsule shaped tablets in a tablet press. The tablets are scored for dividing in half.

EXAMPLE 41

Tablets each containing (S)-1-(3-mercapto-2-methyl-1-oxopropyl)-4-oxo-L-proline and hydrochlorothiazide can be prepared as described in Example 40.

The product of Examples 1,3,5 to 25, and 27 to 29 can be formulated according to the procedures of Examples 32–41.

What is claimed is:

1. A compound of the formula

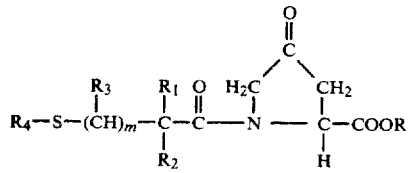

or a physiologically acceptable salt thereof, wherein

R is hydrogen or lower alkyl;

$R_1$ and $R_3$ are independently selected from the group consisting of hydrogen, lower alkyl, lower alkylthio, —$(CH_2)_n$—SH, and halo substituted lower alkyl;

$R_2$ is hydrogen or lower alkyl provided that $R_2$ is lower alkyl only when $R_1$ is lower alkyl;

m is zero, one or two;

n is one, two, or three;

$R_4$ is hydrogen,

p-methoxybenzyl, trityl, or provided that neither $R_1$ nor $R_3$ is —$(CH_2)_n$—SH

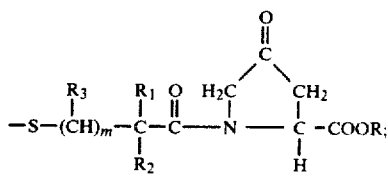

$R_5$ is lower alkyl, chloro, bromo or fluoro substituted lower alkyl, —$(CH_2)_r$—cycloalkyl wherein the cycloalkyl group is a saturated ring of 3 to 7 carbons,

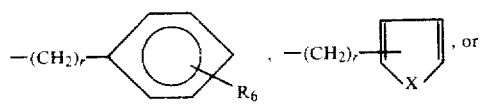 , 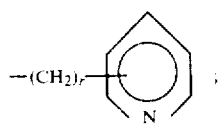 ;

r is zero, one, two, or three;
R$_6$ is hydrogen, lower alkyl of 1 to 4 carbons, lower alkoxy of 1 to 4 carbons, lower alkylthio of 1 to 4 carbons, chloro, bromo, fluoro, trifluoromethyl or hydroxy; and
X is oxygen or sulfur.

2. A compound of the formula

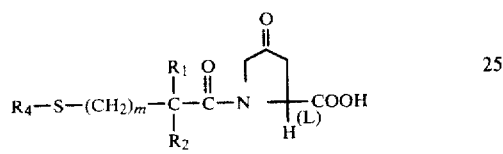

or a physiologically acceptable salt thereof, wherein
R$_1$ and R$_2$ are both lower alkyl of 1 to 4 carbons or
R$_2$ is hydrogen and R$_1$ is hydrogen, lower alkyl of 1 to 4 carbons, trifluoromethyl, methylthio, or mercaptomethyl;
m is zero or one; and
R$_4$ is hydrogen, lower alkanoyl of 1 to 4 carbons, or benzoyl.

3. The compound of claim 2 wherein R$_1$ and R$_2$ are both methyl and m is one.

4. The compound of claim 2 wherein R$_2$ is hydrogen; R$_1$ is trifluoromethyl; and m is one.

5. The compound of claim 2 wherein R$_2$ is hydrogen; R$_1$ is methylthio; and m is one.

6. The compound of claim 2 wherein R$_2$ is hydrogen; R$_1$ is mercaptomethyl; and m is one.

7. The compound of claim 2 wherein R$_1$ and R$_2$ are both hydrogen.

8. The compound of claim 7 wherein m is one.

9. The compound of claim 8 wherein R$_4$ is acetyl.

10. The compound of claim 8 wherein R$_4$ is hydrogen.

11. The compound of claim 7 wherein m is zero.

12. The compound of claim 2 wherein R$_2$ is hydrogen, R$_1$ is methyl, and m is one.

13. The compound of claim 12 wherein R$_4$ is acetyl.

14. The compound of claim 12, wherein R$_4$ is hydrogen.

15. The compound of claim 14, (S)-1-(3-mercapto-2-methyl-1-oxopropyl)-4-oxo-L-proline.

16. A composition useful for treating hypertension comprising a pharmaceutically acceptable carrier and an effective amount of one or more hypotensive agents or physiologically acceptable salts thereof of the formula

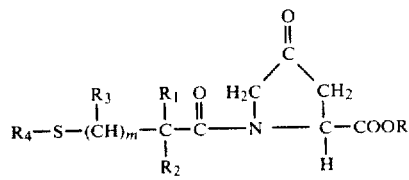

wherein
R is hydrogen or lower alkyl;
R$_1$ and R$_3$ are independently selected from the group consisting of hydrogen, lower alkyl, lower alkylthio, —(CH$_2$)$_n$—SH, and halo substituted lower alkyl;
R$_2$ is hydrogen or lower alkyl provided that R$_2$ is lower alkyl only when R$_1$ is lower alkyl;
m is zero, one, or two;
n is one, two, or three;
R$_4$ is hydrogen,

or provided that neither R$_1$ nor R$_3$ is —(CH$_2$)$_n$—SH

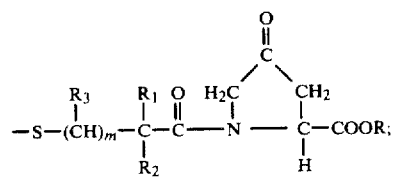

R$_5$ is lower alkyl, chloro, bromo, or fluoro substituted lower alkyl, —(CH$_2$)$_r$—cycloalkyl wherein the cycloalkyl group is a saturated ring of 3 to 7 carbons,

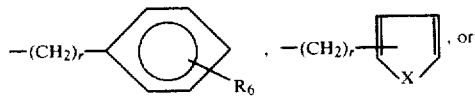 , 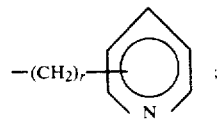 ;

r is zero, one, two, or three;
R$_6$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy; and
X is oxygen or sulfur.

17. The composition of claim 16 wherein the hypotensive agent is of the formula

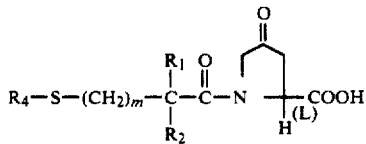

wherein $R_1$ and $R_2$ are both lower alkyl of 1 to 4 carbons or $R_2$ is hydrogen and $R_1$ is hydrogen, lower alkyl of 1 to 4 carbons, trifluoromethyl, methylthio, or mercaptomethyl;

m is zero or one; and $R_4$ is hydrogen, lower alkanoyl of 1 to 4 carbons, or benzoyl.

18. The composition of claim 17 wherein $R_1$, $R_2$, and $R_4$ are hydrogen and m is one.

19. The composition of claim 17 wherein $R_1$ is methyl; $R_2$ and $R_4$ are hydrogen; and m is one.

20. The method of alleviating hypertension which comprises administering an effective amount of the composition of claim 16.

* * * * *